(12) United States Patent
Johnson et al.

(10) Patent No.: US 8,945,607 B2
(45) Date of Patent: Feb. 3, 2015

(54) ELECTROLYTE SUPPLEMENT AND METHOD OF USE

(71) Applicant: Purina Animal Nutrition LLC, Shoreview, MN (US)

(72) Inventors: Thomas Johnson, Thor, IA (US); Bill L. Miller, Labadie, MO (US)

(73) Assignee: Purina Animal Nutrition LLC, Shoreview, MN (US)

( * ) Notice: Subject to any disclaimer, the term of this patent is extended or adjusted under 35 U.S.C. 154(b) by 0 days.

(21) Appl. No.: 14/176,435

(22) Filed: Feb. 10, 2014

(65) Prior Publication Data

US 2014/0255519 A1   Sep. 11, 2014

Related U.S. Application Data

(63) Continuation of application No. 11/331,245, filed on Jan. 12, 2006, now abandoned.

(51) Int. Cl.
| | |
|---|---|
| A23K 1/18 | (2006.01) |
| A01N 59/00 | (2006.01) |
| A61K 33/00 | (2006.01) |
| A61K 31/198 | (2006.01) |
| A61K 31/70 | (2006.01) |
| A61K 31/715 | (2006.01) |
| A61K 33/14 | (2006.01) |
| A61K 33/30 | (2006.01) |
| A61K 45/06 | (2006.01) |
| A61K 33/20 | (2006.01) |

(52) U.S. Cl.
CPC ............... *A61K 31/198* (2013.01); *A61K 31/70* (2013.01); *A61K 31/715* (2013.01); *A61K 33/14* (2013.01); *A61K 33/30* (2013.01); *A61K 45/06* (2013.01); *A61K 33/00* (2013.01); *A61K 33/20* (2013.01)
USPC ........................... 424/438; 424/722; 424/600

(58) Field of Classification Search
CPC .... A61K 33/00; A61K 31/198; A23K 1/1813
USPC .......................................... 424/438, 722, 600
See application file for complete search history.

(56) References Cited

U.S. PATENT DOCUMENTS

| | | |
|---|---|---|
| 3,898,328 A | 8/1975 | Beigler et al. |
| 4,164,568 A | 8/1979 | Bywater |
| 5,200,200 A | 4/1993 | Veech |
| 5,468,224 A | 11/1995 | Souryal |
| 5,962,733 A | 10/1999 | Lall et al. |
| 6,156,333 A | 12/2000 | Langrehr |
| 2003/0143293 A1 | 7/2003 | Shushunov |
| 2004/0137108 A1 | 7/2004 | Abdel-Monem et al. |

*Primary Examiner* — Abigail Fisher
(74) *Attorney, Agent, or Firm* — Dorsey & Whitney LLP; Bridget M. Hayden

(57) ABSTRACT

A method of managing dehydration in an animal includes administering a first electrolyte solution having an SID range at or below 25 mEq/l. After administering the first electrolyte solution, the animal's health condition is observed to determine the effect of the first solution. If the animal's health condition has not sufficiently improved, a second solution comprising the first electrolyte solution supplemented with a second electrolyte supplement is administered to the animal wherein the second electrolyte supplement raises the SID of the second solution to at least 50 mEq/l.

18 Claims, No Drawings

ELECTROLYTE SUPPLEMENT AND METHOD OF USE

BACKGROUND OF THE INVENTION

The present invention relates to feed for an animal. More particularly, the present invention relates to an electrolyte supplement that is orally administered to an animal in an aqueous solution and the method of using the electrolyte supplement.

Young animals such as bovine calves are susceptible to diarrhea. Diarrhea are caused by a number of infectious agents including bacteria such as *Escherichia coli, salmonella* species, viruses such as Rotavirus, Coronavirus, and Torovirus and other pathogens. Each of these pathogens causes symptoms including dehydration, acidosis, electrolyte abnormalities and hyperglycemia. In the case of severe diarrhea, a young calf may suffer permanent internal injuries which may result in lower weight gain and/or milk production as an adult mammal. In some instances, severe diarrhea can result in the death of a young animal.

Aqueous supplements containing simple carbohydrates, such as glucose, fructose and/or dextrose, and electrolytes can be given to the calves with diarrhea to treat the symptoms caused by diarrhea, namely dehydration, acidosis, lack of energy and a reduction in electrolyte levels. There are several aqueous electrolyte supplements that are currently being fed to calves including supplements containing electrolyte concentrations of less than 20 strong ion difference (SID). The SID of a solution is determined by adding the mEq/l of sodium ion with the mEq/l of potassium ion and subtracting the mEq/l of chloride ion. An electrolyte supplement having a SID of 20 or less is considered to be "weak" by industry standards. In some instances, "weak" electrolyte supplements provide adequate amounts of water, simple carbohydrates and electrolytes to treat the symptoms associated with diarrhea. However, if the calf has a severe case of diarrhea, a "weak" electrolyte supplement may not provide an adequate remedy for the young animal to reverse the effects of diarrhea.

When a "weak" electrolyte supplement does not provide an adequate remedy for diarrhea, a "strong" aqueous electrolyte supplement may be orally administered to the calf. "Strong" electrolyte supplements have ion concentrations of between about 50 and about 80 SID. "Strong" electrolyte supplements generally replenish electrolyte levels in the calf and remedy the calf's other symptoms associated with diarrhea.

However, "strong" electrolyte supplements typically contain ingredients that address virtually every symptom associated with diarrhea which may not be necessary to cure a particular calf of diarrhea. Because "strong" electrolyte supplements are designed to treat virtually every symptom associated with diarrhea, "strong" electrolyte supplements are expensive relative to "weak" electrolyte supplements. Because of the difference in cost, the producer is left with a decision of feeding the calf a "strong" supplement that will reduce the effect of diarrhea but will cost a significant amount of money or feeding the calf a "weak" supplement which costs considerably less money but may or may not improve the dehydration caused by diarrhea.

SUMMARY OF THE INVENTION

The present invention includes a method of managing dehydration in an animal which includes administering a first aqueous electrolyte solution to the animal having a SID range at or below 25 mEq/l. After administering the first aqueous electrolyte solution, the animal's health is observed to determine the effect of the first electrolyte solution. A second aqueous electrolyte solution may be administered to the animal based on the animal's health conditions where the second solution comprises the first electrolyte solution supplemented with electrolyte components that raise the SID of the second aqueous electrolyte solution to at least 50 mEq/l.

DETAILED DESCRIPTION OF THE INVENTION

The present invention includes an aqueous electrolyte supplement that is fed to young animals, and preferably young bovine calves, to prevent the dehydration caused by diarrhea, shipping and hot weather. The electrolyte supplement includes a base electrolyte supplement that mixes into a selected amount of water for oral administration of dehydrated calves. Depending upon the results of the base solution on the symptoms of diarrhea, an additional electrolyte supplement can be added to the base solution to increase the electrolyte concentration of the supplement to a "strong" solution which is orally administered to the calf.

The base electrolyte supplement and the additional electrolyte supplement are preferably in powder form prior to use. However the base electrolyte supplement and the additional electrolyte can be provided in a concentrated aqueous form or a ready to use solution.

The base electrolyte supplement contains selected amounts of simple carbohydrates and electrolytes including but not limited to, salts of sodium, potassium and chloride. A selected amount of the base electrolyte supplement is added to a selected amount of water such that salts disassociate to produce a base solution with a SID of preferably less than or equal to 25 mEq/l. While a SID concentration of less than or equal to 25 is preferred, the aqueous base solution may have a SID of up to and including 35.

The simple carbohydrate is preferably dextrose which the calf quickly processes to provide a quick supply of energy. Other simple carbohydrates or sugars such as, but not limited to, glucose and fructose may also be added to the base to provide a readily accessible supply of energy. While providing readily accessible energy, the simple carbohydrate also helps with the transport of sodium ions within the young animal.

The sodium ions aid in absorbing the water into the young animal's body to combat dehydration. The potassium ions and the chloride ions are included in the base solution to replace the ions lost due to the diarrhea. The preferred ranges of the ingredients for the base electrolyte supplement follows in Table 1:

TABLE 1

| Ingredient | Preferred Weight % | Range Weight % |
| --- | --- | --- |
| Sodium | 5.6 | 3.5-10.0 |
| Chloride | 8.35 | 5.0-15.0 |
| Potassium | 1.98 | 0.5-5.0 |
| Dextrose | 75 | 50-90 |
| Gum | 0.75 | 0.1-1.5 |

The sodium is provided in a salt form including, but not limited to, sodium chloride, sodium citrate and monosodium phosphate. The chloride is added in a salt form, including, but not limited to, sodium chloride and potassium chloride. The potassium is added in a salt form including, but not limited to, potassium chloride, potassium citrate and potassium phosphate. The phosphate ion and the citrate ions are not accounted for in Table 1. However, an electrolyte solution having the above weight percentage is within the scope of the present invention.

The gum is optionally added to retain the ingredients in suspension in the base solution and to slow the rate of freezing. However, the gum is not necessary to practice the present invention. The gum can include xanthan gum, processed guar gum and hemicellulose extract or any combination thereof. Other suspension agents are also within the scope of the present invention.

After orally administering the aqueous base solution to the calf, the calf's physical condition is monitored to determine whether the calf's physical condition is improving over time. The calf's symptoms show improvement when the severity of the diarrhea normalizes the calf's energy increases and/or the calf's temperature decreases.

When the calf shows improvement, the base solution will continue to be orally administered to the calf until the calf improves such that the base solution is not necessary to improve the calf's physical condition. However, if the calf's physical condition does not improve using the base solution alone as an aqueous electrolyte supplement, the additional electrolyte supplement is added to the base solution which is subsequently orally administered to the calf.

The additional electrolyte supplement, which may alternatively be referred to as an "add pack", includes an effective amount of glycine that allows the calf to utilize the simple carbohydrate and sodium more efficiently than an electrolyte supplement that does not contain glycine.

A selected amount of sodium bicarbonate is also included in the additional electrolyte supplement in an amount effective to control acidosis. Sodium bicarbonate dissociates into a base or an alkalynizing agent in an aqueous solution that aids in controlling acidosis. However, other bases or alkalynizing agents which are generally recognized as (GRAS) safe for the calf to ingest are also within the scope of the present invention.

The additional electrolyte supplement also includes another effective amount of sodium preferably in a salt form. The sodium salt dissociates into its ionic form in an aqueous solution. The sodium in the additional electrolyte supplement is in the form of a salt including, but not limited to, sodium bicarbonate, sodium citrate, and sodium acetate.

The additional electrolyte supplement includes at least the following ingredients listed in Table 2. However, other ingredients may be included in the additional electrolyte supplement while practicing the present invention.

TABLE 2

| Ingredient | Preferred Weight % | Weight % |
| --- | --- | --- |
| Glycine | 53.2 | 40.0-60.0 |
| Sodium Bicarbonate | 42.5 | 25.0-50.0 |

The additional electrolyte solution is not fed directly to the dehydrated calf, but orally administered as a supplement to the aqueous base solution. The aqueous supplement, having the additional electrolyte supplement added to the base solution forms a "strong" solution having about 64.4 mEq/l. However the strong solution of the present invention may have a SID in a range of between about 50 and about 80. Table 3 is a tabulation of the concentrations of the critical ingredients in powdered form of the combined base electrolyte supplement and additional electrolyte supplement that are mixed into a selected amount of water to form the strong electrolyte solution of the present invention.

TABLE 3

|  | Preferred Weight % | Weight % |
| --- | --- | --- |
| Ingredient Inclusion |  |  |
| Dextrose | 60.0 | 50.0-90.0% |
| Glycine | 9.4 | 5.0-12.0% |
| Sodium Bicarbonate | 7.7 | 5.0-10.0% |
| Gum | 0.62 | 0.4-0.9% |
| Product Specification |  |  |
| Sodium | 6.59 | 5.0-9.0% |
| Chloride | 6.84 | 5.0-9.0% |
| Potassium | 1.63 | 0.7-2.3% |
| SID | 64.4 | 50-80 mEq/l |

The strong aqueous solution is orally administered to the calf to remedy diarrhea. However, while remedying diarrhea, the additional ingredients also significantly increase the cost of the electrolyte supplement. Therefore, initially administering the base solution provides a cost-effective method for attempting to remedy diarrhea and its symptoms. If the base solution does not adequately remedy diarrhea or does not cause improvement in the calf's condition, the additional electrolyte supplement is added to the base solution containing the base electrolytes. The additional electrolyte supplement includes the more expensive ingredients such as glycine and sodium bicarbonate which increases the cost of combating diarrhea in a calf while resulting in the improvement of the calf's physical condition.

The ingredients of the base electrolyte supplement and the additional electrolyte supplement both mix into water without changing the color of the water. If more than one container is being utilized, the person tending to the calves may become confused whether the base electrolyte supplement has been added to the water to form the base solution and/or whether the additional electrolytic supplement has been added to the base solution to form the strong solution. To remedy the lack of color, a GRAS dye is optionally but typically added to both the base electrolyte supplement and to the additional electrolyte supplement.

Typically, when the base electrolyte supplement is mixed into water, the base solution turns a distinguishing color such as yellow. While yellow is a typical color because it is easily viewed, other colors for the base solution are within the scope of the present invention.

When the additional electrolyte supplement is added to the base solution, the additional electrolyte supplement turns the "strong" SID solution to a different color than the color of the aqueous base solution. Typically, when the additional electrolyte supplement is added to the "weak" base solution, the solution changes from a yellow color to an orange color. By adding different dyes to both the base electrolyte supplement and the additional electrolyte supplement, the administrant of the electrolyte supplement will be readily able to ascertain whether the container contains water, the "weak" electrolyte supplement or the "strong" electrolyte supplement.

The base solution optionally includes a suspension agent or mixture of suspension agents that prevent insoluble ingredients or soluble ingredients at saturation concentrations from settling out of the aqueous solution over time and to slow rate of freezing. While the suspension agent is not necessary to practice the present invention, the suspension agent maintains the ingredients in suspension in the aqueous solution such that the particles are substantially evenly dispersed within the aqueous solution. A typical suspension agent is a gum or combination of gums. The typical gums are xanthan gum, guar gum and hemicellulose extract or any combination thereof. Other suspension agents are also within the scope of the present invention.

The suspension agent allows non-soluble ingredients to be added to the electrolytes supplement, such as zinc oxide, kaolin, pectin, and activated charcoal. Zinc oxide is known to be used successfully in the farm industry to reduce diarrhea when fed to swine in nursery diets. However, zinc oxide is insoluble in water and quickly settles out of an aqueous solution which limits the effectiveness of zinc oxides in threatening diarrhea in bovine calves. It has been discovered that the gum or combination of gums adequately suspends an amount of zinc oxide in solution that is effective to treat diarrhea when ingested by calves. Zinc oxide can be included in the base electrolyte solution in concentrations up to 10,000 ppm. The effect of zinc oxide being included with the base solution was tested on calves having diarrhea.

Trial 1

Sixty-two calves that were 3 to 10 days of age weighing an average of 100 pounds were purchased through sale barns in Wisconsin. Each of the calves had diarrhea and were observed to determine the effectiveness of the addition zinc oxide to the base solution in treating diarrhea. The calves were fed a standardized milk replacer diet. Diarrhea scores were taken daily. Thirty-one calves received the base solution without zinc oxide and the other thirty-one calves received the base solution with zinc oxide. Both sets of calves were provided the base solution as needed for diarrhea and dehydration. The results of the experiment are listed below in Table 4.

TABLE 4

| Item | Base Solution Without ZnO[A] | Base Solution With ZnO[B] |
|---|---|---|
| No. of Calves | 31 | 31 |
| Ave. Diarrhea Score[C] | 2.10 | 2.08 |
| Total Diarrhea Days[D] | 6.77 | 6.16 |
| Diarrhea Severity Index[E] | 14.27 | 12.98 |

[A]Base solution without ZnO.
[B]Base solution with 5000 ppm ZnO.
[C]Diarrhea Score = 1-4 scale; 1 = normal, 2 = loose, 3 = water separation, 4 = 3 with severe dehydration. For this evaluation, only calves with a diarrhea score of 2 or higher were included.
[D]Diarrhea Days calculated by totaling the days that calves had a diarrhea score of 2 or higher.
[E]Diarrhea Severity Index places a value on intensity of the diarrhea combined with the duration of diarrhea days. Diarrhea Severity Index is calculated by multiplying the Average Diarrhea Score by the Total Diarrhea Days.

The results of the experiment showed that calves ingesting the base solution with zinc oxide had lower diarrhea scores, fewer diarrhea days and lower diarrhea severity index. In conducting this trial, gum suspension agents were included in the base solution to retain zinc oxide in solution.

Trial 2

A trial was performed to determine the effectiveness of the base solution with zinc oxide performed in comparison to Merrick's Blue Ribbon electrolyte supplement manufactured by Merrick's, Inc. of Middleton, Wis. In the trial, 55 calves between 3 and 10 days of age weighing an average of about 100 pounds were purchased from sale barns in Wisconsin and were evaluated. Only calves with diarrhea were evaluated where the calves were fed a standardized milk replacer diet. Thirty-three calves ingested the base solution of the present invention with zinc oxide as needed for diarrhea and dehydration and thirty-two calves ingested Merrick's Blue Ribbon electrolyte supplement as needed for diarrhea and dehydration. Diarrhea scores were taken daily. The performance of the calves consuming the "weak" SID electrolyte supplement of the present invention with zinc oxide and the calves fed Merrick's Blue Ribbon electrolyte supplement are listed as follows:

TABLE 5

| Item | Base W/ZnO[A] | Merrick's Blue Ribbon[B] | P-value | C.V |
|---|---|---|---|---|
| No. of Calves | 33 | 32 | | |
| Ave. Diarrhea Score[C] | 2.12 | 2.14 | 0.04905 | 6.30 |
| Total Diarrhea Days[D] | 7.15 | 9.09 | 0.0575 | 49.89 |
| Diarrhea Severity Index[E] | 15.38 | 19.75 | 0.0610 | 52.69 |

[A]Base solution containing 0.5% Zinc Oxide (5000 ppm).
[B]Merrick's Blue Ribbon, Non-Gelling, commercial product, Merrick's Inc. of Middleton, Wisconsin.
[C]Diarrhea Score = 1-4 scale; 1 = normal, 2 = loose, 3 = water separation, 4 = 3 with severe dehydration. For this electrolyte evaluation, only calves with a diarrhea score of 2 or higher were included.
[D]Diarrhea Days were calculated by totalling all days calves had a diarrhea score of 2 or higher.
[E]Diarrhea Severity Index puts a value on intensity of the diarrhea combined with the duration of diarrhea days. Diarrhea Severity Index was calculated by multiplying the Average Diarrhea Score by the Total Diarrhea Days.

The results of this trial showed that the base with zinc oxide reduced diarrhea days and diarrhea severity index as compared to an electrolyte supplement without zinc oxide.

Trial 3

A trial was conducted to determine the palatability of the base solution with the zinc oxide as compared to Merrick's Blue Ribbon electrolyte supplement and Re-sorb.® electrolyte supplement manufactured by Pfizer, Inc. of New York, N.Y. Sixteen calves between 3 and 10 days of age weighing an average of about 100 pounds were purchased from sale barns in Wisconsin and were evaluated in the trial. The calves had diarrhea and were fed a standardized milk replacer diet. Only calves that were trained to drink out of a pail were utilized in the trial. Eight calves were chosen per comparison where one pail of the base solution with zinc oxide and one pail of the commercially available electrolyte system were offered side by side to each of the calves. The calves were given an equal time to choose between the base solution with zinc oxide and the other commercially available electrolyte supplements. A total of four offerings were given over two days with a minimum of 8 hours between offerings. The results are as follows in Table 6.

TABLE 6

| Product Description | Consumption Lbs/fdg (solution) | Preference Ratio[A] | P-value | Preference Incidence[B] |
|---|---|---|---|---|
| Base[C] with ZnO | 2.12 | 1.14:1.00 | 0.3107 | 34 |
| Re-sorb ®[D] electrolyte supplement | 1.85 | | | 22 |
| Base w/ZnO | 1.15 | 1.15:1.00 | 0.4926 | 25 |
| Mericks Blue Ribbon[E] electrolyte supplement | 1.33 | | | 31 |

[A]Determined by dividing the intake of the preferred product by that of the less preferred product.
[B]Percentage of feedings that calves preferred each product. Total does not Equal 100 due to ties.
[C]Base solution contained 0.5% Zinc Oxide (5000 ppm).
[D]Re-sorb ® commercial product manufactured by Pfizer, Inc. of New York, New York.
[E]Merrick's Blue Ribbon, Non-Gelling, commercial product, manufactured by Merrick's Inc. of Middleton, Wisconsin.

The results show that there was a statistically equal preference for both the base solution with zinc oxide and the commercially available electrolyte supplements. The results indicate that the inclusion of zinc oxide at 5000 ppm does not hinder the palatability of the electrolyte system while the previous trials indicate that zinc oxide increases the effectiveness of the electrolyte supplement in reducing diarrhea.

Trial 4

A trial was conducted to determine the costs of using the base solution of the present system with zinc oxide as compared to Merrick's Blue Ribbon electrolyte supplement. In the trial, fifty-five calves between 3 and 10 days of age weighing an average of about 100 pounds were purchased from sale barns in Wisconsin and were evaluated. The calves were fed a standardized milk replacer diet where only calves with diarrhea were used during the trial. Diarrhea scores were taken daily. Thirty-three of the calves received the base solution with zinc oxide and thirty-two calves received Merrick's Blue Ribbon electrolyte supplement as needed for diarrhea and dehydration. The cost the of electrolyte supplement per calf was calculated including the cost of freight. The results of the trial are as follows:

TABLE 7

| Item | Base w/ZnO[A] | Merrick's Blue Ribbon[B] | P-value | C.V. |
|---|---|---|---|---|
| No. of Calves | 33 | 32 | | |
| "Base" Electrolyte Cost[C] | 4.07 | 10.46 | 0.0001 | 72.24 |
| "AddPack" Electrolyte Cost[D] | 0.42 | — | — | — |
| Total Cost Per Calf[E] | 4.49 | 10.46 | 0.0001 | 60.41 |

[A]Base solution containing 0.5% Zinc Oxide (5000 ppm).
[B]Merrick's Blue Ribbon, Non-Gelling, commercial product manufactured by Merrick's Inc. of Middleton, Wisconsin.
[C]"Base" cost/dose mimicked retail pricing F.O.B. farm. Base = $0.29/dose and Merrick's Blue Ribbon = $0.57/dose.
[D]"Add Pack" cost/dose mimicked retail pricing F.O.B. to location of experiment = $0.28. Merrick's Blue Ribbon is formulated complete so no Add Pack was ever added.
[E]Total Electrolyte Cost is "Base" + "Add Pack" (if used).

The results of the trial indicate that the base with zinc oxide including the additional electrolyte supplement indicated by the term "Add Pack" was more cost effective than Merrick's Blue Ribbon electrolyte supplement. The cost per calf using the electrolyte solution with zinc oxide and the "Add Pack" was less than half of the cost per calf when compared to using Merrick's Blue Ribbon electrolyte supplement. Significant economic savings were realized by utilizing the base solution with zinc oxide and the "Add Pack" of the present invention to minimize the effects of diarrhea and dehydration.

Trial 5

A trial was conducted to determine the costs of using the base of the present system with zinc oxide and the Add Pack as compared to Pfizer's Re-sorb® electrolyte supplement. Fifty-one calves, 3 to 10 days of age and weighing an average of 100 pounds, were purchased from sale barns in Wisconsin and were evaluated. During the trial, 27 calves were fed the base solution with zinc oxide and 24 of the calves were fed the Re-sorb® electrolyte system. Only calves with diarrhea were used during the trial and the calves were fed standardized milk replacer diet. Diarrhea scores were taken daily. Retail costs were calculated and included freight costs to the location of the trial.

TABLE 8

| Item | Base w/ZnO[A] | Resorb[B] | P-value | C.V. |
|---|---|---|---|---|
| No. of Calves | 27 | 24 | | |
| "Base" Electrolyte Cost[C] | 2.93 | 16.24 | 0.0001 | 91.95 |
| "Add Pack" Electrolyte Cost[D] | 0.18 | — | — | — |
| Total Cost Per Calf[E] | 3.11 | 16.24 | 0.0001 | 85.16 |

[A]Base solution contained 0.5% Zinc Oxide (5000 ppm).
[B]Re-sorb ®, commercial product, manufactured by Pfizer, Inc. of New York, New York.
[C]"Base" cost/dose mimicked retail pricing F.O.B. base solution w/ZnO = $0.29 and Re-sorb ®, = $1.78/dose.
[D]"Add Pack" cost/dose mimicked retail pricing F.O.B. = $0.28/dose. Re-sorb ® electrolyte system is formulated complete so no "Add Pack" was ever added.
[E]Total Electrolyte Cost is "Base" + "Add Pack" (if used).

The base solution with zinc oxide including the "Add Pack" electrolyte system cost a total of about $3.11 per calf while Pfizer's Re-sorb® electrolyte supplement cost on average $16.24 per calf. The trial indicated that using the base solution with zinc oxide of the present invention with the "Add Pack" or additional electrolyte system saves approximately $13.13 per calf when compared to the cost of using Pfizer's Re-sorb® electrolyte supplement. The trial also indicated that utilizing the base solution with zinc oxide resulted in a statistically significant reduction in cost when compared to the Re-sorb® electrolyte supplement.

Trial 8

A trial was run to determine the effectiveness of a suspension agent on the suppression of the freezing point of the base solution. Suppressing the freeze point is beneficial when feeding the electrolyte system to calves in an outdoor environment in colder climates. The base solution is typically made available to the calves in a pail for an extended period of time at or below freezing temperature. In colder climates, the aqueous electrolyte base solution has a tendency of forming an ice layer on the surface thereby making the electrolyte system undrinkable for the calf.

A comparison was conducted by mixing 77 grams of the base electrolyte supplement without and with the suspension agents separately into two quarts of water at a temperature of 111.3° F. The base electrolyte system was mixed into the water for about 15 seconds with a whisk in a black 10-quart calf pail after which the electrolyte solutions were allowed to sit for 5 minutes. Both solutions were remixed with a whisk and then placed side by side in a walk-in freezer maintained at about 5° F. The results of the trial are as follows.

TABLE 9

| Hour | Base Solution w/o Suspension Ingredient | | Base Solution with suspension Ingredient | |
|---|---|---|---|---|
| | ° F. | Comments | ° F. | Comments |
| 0.0 | 101 | | 101 | |
| 0.5 | 76 | | 88 | |
| 1.0 | 65 | | 76 | |
| 1.5 | 50 | | 61 | |
| 2.0 | 43 | | 56 | 2 mm ice crystals along inside pail rim |
| 2.5 | 36 | | 49 | 2 mm ice crystals along inside pail rim |
| 3.0 | 22 | Slushy ice layer across | 45 | 1.5 cm ice crystals along inside pail rim |
| 3.3 | — | Solid ice layer across | | |
| 3.5 | — | Solid ice layer across | 38 | 2.5 cm ice crystals along inside pail rim |

TABLE 9-continued

| | Base Solution w/o Suspension Ingredient | | Base Solution with suspension Ingredient | |
|---|---|---|---|---|
| Hour | °F. | Comments | °F. | Comments |
| 4.0 | — | Solid ice layer across | 37 | 5 cm ice crystals along inside pail rim |
| 4.5 | — | Solid ice layer across | 34 | 6 cm ice crystals along inside pail rim |
| 5.0 | — | Solid ice layer across | 31 | Slushy ice layer across |
| 5.08 | — | Solid ice layer across | — | Solid ice layer across |

The results of the trial indicate that the electrolyte system without suspension formed a solid ice layer across the surface in about 3.3 hours while the electrolyte system with the suspension agent formed a solid ice layer across the surface in about 5.08 hours. While wishing to not be bound by theory, applicants believe that the increased time needed to form a solid ice layer caused by the suspension agent was the result of retaining more ions in solution and thereby suppressing the freezing point of the base solution. Especially in cold climates where calves can be fed in outdoor conditions at temperatures below freezing, suppressing the freeze point of the solution provides a benefit in increasing the effectiveness of the electrolyte system because the calf has a longer time period to consume the aqueous electrolyte system.

It is believed that once the electrolyte system has a solid layer across the surface of the solution, the calves will be unable to consume the electrolyte system. Therefore, the addition of the gum suspension ingredients allow the calves more time to consume the electrolyte system which increases the effectiveness of the electrolyte solution and counteracting the effects of diarrhea.

Data for parameters presented in the Tables above was analyzed using the general linear model (GLM) statistical procedure of SAS/STAT. Statistical analysis software for a randomized complete block design that included both the particular feed regimen and the week of the test period in the model statement. The SAS/STAT statistical analysis software is available from SAS Institute, Inc. of Cary, N.C. Additionally, all data was analyzed to determine the mean of the data for each variable under consideration during the collection period for the particular data.

Additionally, the PDiff function of the GLM statistical procedure was used to characterize the mean values of the data by providing for comparisons between mean data values for the calves of different treatments for particular test parameters or variables.

P used in the Tables above is a probability value. For purposes of comparing data in this document, P values of 0.10, or lower, are considered to be statistically significant.

Also, the Tables include a coefficient of variation (CV) for data in a particular row. The coefficient of variation is the standard deviation of a particular variable divided by the mean of the variable and then multiplied by 100.

Although the present invention has been described with reference to preferred embodiments, workers skilled in the art will recognize that changes may be made in form and detail without departing from the spirit and scope of the invention.

What is claimed is:

1. A method of treating dehydration in an animal, the method comprising
administering to an animal a first electrolyte solution having an SID equal to or less than 25 mEq/l wherein the first electrolyte solution is free of glycine and alkalinizing agents;
observing the animal's health condition to determine the effect of the first electrolyte solution; and
where the animal's health condition has not improved:
combining an additional amount of the first electrolyte solution with an electrolyte supplement comprising glycine and one or more alkalynizing agents to form a second electrolyte solution, wherein the second electrolyte solution has an SID of at least 50 mEq/l, and administering the second electrolyte solution to the animal.

2. The method of claim 1 wherein improvement in the animal's health condition comprises one or more of normalization of the severity of diarrhea, increase in the animal's energy, or decrease of the animal's temperature.

3. The method of claim 1 wherein the first and second electrolyte solutions are administered orally.

4. The method of claim 1 wherein the dehydration is caused by diarrhea, shipping, or hot weather.

5. The method of claim 1 wherein the first electrolyte solution has a first color, and the combining of the electrolyte supplement with the additional amount of the first electrolyte solution causes the second electrolyte solution to have a second color that is different from the first color.

6. The method of claim 1 wherein the electrolyte supplement is not fed directly to the animal.

7. The method of claim 1 wherein the first electrolyte solution further comprises one or more of dextrose, glucose, and fructose.

8. The method of claim 1 wherein the first electrolyte solution further comprises a gum.

9. The method of claim 1 wherein the electrolyte supplement comprises sodium bicarbonate, sodium acetate, or sodium citrate, or a combination thereof.

10. The method of claim 1 wherein the first electrolyte solution is formed by mixing an electrolyte powder with water prior to the administering; and wherein the electrolyte supplement is a powder that is mixed with the first electrolyte solution to form the second electrolyte solution.

11. The method of claim 1 wherein the animal is a calf.

12. A method of treating dehydration in a calf, the method comprising
forming a first electrolyte solution comprising water and about 3.5 wt % to 10.0 wt % sodium based on component dry weight, about 5.0 wt % to 15.0 wt % chloride based on component dry weight, about 0.5 wt % to 5.0 wt % potassium based on component dry weight, and about 50 wt % to 90 wt % dextrose based on component dry weight wherein the first electrolyte solution is free of glycine and alkalinizing agents;
orally administering the first electrolyte solution to a dehydrated calf;
monitoring the effect of the first electrolyte solution by observing one or more symptoms comprising severity of diarrhea, the calf's energy, and the calf's temperature; and
where one or more of the symptoms have not improved, orally administering to the calf a second electrolyte solution, the second electrolyte solution comprising the first electrolyte solution combined with an electrolyte supplement such that the electrolyte supplement is not fed directly to the animal, the electrolyte supplement comprising about 40.0 wt % to 60.0 wt % glycine based on component dry weight of the electrolyte supplement and about 25.0 wt % to 50.0 wt % of an alkalynizing agent based on component dry weight of the electrolyte supplement, wherein the second electrolyte solution has an SID of at least 50 mEq/l.

13. The method of claim 12 wherein the dehydration is caused by diarrhea, shipping, or hot weather.

14. The method of claim 12 wherein the first electrolyte solution has an SID of 25 mEq/l or less.

15. The method of claim 12 wherein the first electrolyte solution further comprises a gum.

16. The method of claim 15 wherein the gum is xanthan gum.

17. The method of claim 12 wherein the electrolyte supplement comprises sodium bicarbonate, sodium acetate, or sodium citrate, or a combination thereof.

18. The method of claim 12 wherein the first electrolyte solution has a first color, and the second electrolyte solution has a second color that is different from the first color.

* * * * *

UNITED STATES PATENT AND TRADEMARK OFFICE
CERTIFICATE OF CORRECTION

| | |
|---|---|
| PATENT NO. | : 8,945,607 B2 |
| APPLICATION NO. | : 14/176435 |
| DATED | : February 3, 2015 |
| INVENTOR(S) | : Thomas Johnson et al. |

It is certified that error appears in the above-identified patent and that said Letters Patent is hereby corrected as shown below:

SPECIFICATION

| Column | Line | PTO | Should Be |
|---|---|---|---|
| 3 | 17 | "When the calf' shows" | -- When the calf shows -- |
| 6 | 32 | "and Re-sorb.®" | -- and Re-sorb ® -- |

Signed and Sealed this
Nineteenth Day of May, 2015

Michelle K. Lee
*Director of the United States Patent and Trademark Office*